United States Patent
Embry et al.

(10) Patent No.: US 7,799,078 B2
(45) Date of Patent: Sep. 21, 2010

(54) IMPLANTABLE VERTEBRAL LIFT

(75) Inventors: Jill M. Embry, Somerville, TN (US); Robert J. Boock, San Diego, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1558 days.

(21) Appl. No.: 10/987,180

(22) Filed: Nov. 12, 2004

(65) Prior Publication Data

US 2006/0106461 A1    May 18, 2006

(51) Int. Cl.
*A61F 2/44* (2006.01)
*A61B 17/58* (2006.01)
(52) U.S. Cl. .................................. 623/17.11; 606/94
(58) Field of Classification Search ... 623/17.11–17.16, 623/16.11, 11.11; 606/191–198, 92–94, 606/61, 151, 99
See application file for complete search history.

(56) References Cited

U.S. PATENT DOCUMENTS

| | | | | |
|---|---|---|---|---|
| 4,865,604 A | * | 9/1989 | Rogozinski | 623/23.42 |
| 5,059,193 A | * | 10/1991 | Kuslich | 606/247 |
| 5,090,957 A | * | 2/1992 | Moutafis et al. | 600/18 |
| 5,108,404 A | * | 4/1992 | Scholten et al. | 606/94 |
| 5,480,400 A | | 1/1996 | Berger | |
| 5,549,679 A | * | 8/1996 | Kuslich | 623/17.12 |
| 5,645,597 A | * | 7/1997 | Krapiva | 606/279 |
| 5,827,289 A | * | 10/1998 | Reiley et al. | 606/86 R |
| 5,827,314 A | | 10/1998 | Lunsford et al. | |
| 5,865,802 A | | 2/1999 | Yoon et al. | |
| 5,868,779 A | | 2/1999 | Ruiz | |
| 5,928,260 A | * | 7/1999 | Chin et al. | 606/200 |
| 5,964,770 A | | 10/1999 | Flomenblit et al. | |
| 5,972,015 A | * | 10/1999 | Scribner et al. | 606/192 |
| 6,027,744 A | | 2/2000 | Vacanti et al. | |
| 6,048,346 A | * | 4/2000 | Reiley et al. | 606/92 |
| 6,066,154 A | * | 5/2000 | Reiley et al. | 606/192 |
| 6,127,597 A | * | 10/2000 | Beyar et al. | 606/86 R |
| 6,171,610 B1 | | 1/2001 | Vacanti et al. | |
| 6,235,043 B1 | | 5/2001 | Reiley et al. | |
| 6,248,110 B1 | | 6/2001 | Reiley et al. | |
| 6,261,289 B1 | | 7/2001 | Levy | |
| 6,280,456 B1 | * | 8/2001 | Scribner et al. | 606/192 |
| 6,299,448 B1 | | 10/2001 | Zdrahala et al. | |
| 6,332,894 B1 | * | 12/2001 | Stalcup et al. | 623/17.11 |

(Continued)

FOREIGN PATENT DOCUMENTS

WO    WO 01/28461 A2    4/2001

(Continued)

*Primary Examiner*—Alvin J. Stewart
(74) *Attorney, Agent, or Firm*—Haynes and Boone, LLP

(57) ABSTRACT

A vertebral lift device including an expandable member made of a bio-compatible material and having a plurality of interconnected structural members, with the expandable member having a first dimension for insertion thereof into a damaged vertebral body having a damaged dimension, the interconnected structural members of the expandable member being expandable to a second dimension substantially corresponding to dimensions of the vertebral body prior to its damage, wherein the expandable member defines a void area within a periphery defined by the structural members when the expandable member is expanded to the second dimension for receiving a restoration agent; and a covering configured to substantially cover the exterior of the expandable member to inhibit leakage of the restoration agent received within the void area.

12 Claims, 16 Drawing Sheets

U.S. PATENT DOCUMENTS

| | | | |
|---|---|---|---|
| 6,423,083 B2 * | 7/2002 | Reiley et al. | 606/192 |
| 6,440,138 B1 | 8/2002 | Reiley et al. | |
| 6,554,833 B2 | 4/2003 | Levy et al. | |
| 6,582,446 B1 * | 6/2003 | Marchosky | 606/167 |
| 6,582,467 B1 * | 6/2003 | Teitelbaum et al. | 623/17.11 |
| 6,607,544 B1 * | 8/2003 | Boucher et al. | 606/192 |
| 6,620,162 B2 * | 9/2003 | Kuslich et al. | 606/53 |
| 6,623,505 B2 * | 9/2003 | Scribner et al. | 606/192 |
| 6,632,235 B2 * | 10/2003 | Weikel et al. | 606/192 |
| 6,641,587 B2 | 11/2003 | Scribner et al. | |
| 6,663,647 B2 | 12/2003 | Reiley et al. | |
| 6,676,665 B2 * | 1/2004 | Foley et al. | 606/105 |
| 6,679,886 B2 | 1/2004 | Weikel et al. | |
| 6,706,069 B2 * | 3/2004 | Berger | 623/17.12 |
| 6,712,853 B2 * | 3/2004 | Kuslich | 623/17.16 |
| 6,716,216 B1 | 4/2004 | Boucher et al. | |
| 6,719,773 B1 | 4/2004 | Boucher et al. | |
| 6,726,691 B2 * | 4/2004 | Osorio et al. | 606/94 |
| 6,726,721 B2 * | 4/2004 | Stoy et al. | 623/17.16 |
| 6,740,093 B2 * | 5/2004 | Hochschuler et al. | 606/94 |
| 6,958,077 B2 * | 10/2005 | Suddaby | 623/17.11 |
| 6,979,341 B2 * | 12/2005 | Scribner et al. | 606/192 |
| 7,077,865 B2 * | 7/2006 | Bao et al. | 623/17.12 |
| 7,226,481 B2 * | 6/2007 | Kuslich | 623/17.11 |
| 7,238,209 B2 * | 7/2007 | Matsuzaki et al. | 623/23.61 |
| 7,465,318 B2 * | 12/2008 | Sennett et al. | 623/17.12 |
| 7,534,268 B2 * | 5/2009 | Hudgins et al. | 623/17.12 |
| 7,537,616 B1 * | 5/2009 | Branch et al. | 623/17.16 |
| 2002/0026197 A1 * | 2/2002 | Foley et al. | 606/105 |
| 2002/0058947 A1 | 5/2002 | Hochschuler et al. | |
| 2002/0068974 A1 | 6/2002 | Kuslich et al. | |
| 2002/0183761 A1 * | 12/2002 | Johnson et al. | 606/90 |
| 2003/0109883 A1 | 6/2003 | Matsuzaki et al. | |
| 2004/0024463 A1 | 2/2004 | Thomas, Jr. et al. | |
| 2004/0073308 A1 * | 4/2004 | Kuslich et al. | 623/17.11 |
| 2004/0097930 A1 * | 5/2004 | Justis et al. | 606/61 |
| 2004/0097980 A1 * | 5/2004 | Ferree | 606/151 |
| 2004/0102774 A1 * | 5/2004 | Trieu | 606/61 |
| 2004/0220615 A1 * | 11/2004 | Lin et al. | 606/232 |
| 2004/0230309 A1 * | 11/2004 | DiMauro et al. | 623/17.12 |
| 2005/0090901 A1 * | 4/2005 | Studer | 623/17.12 |
| 2005/0192662 A1 * | 9/2005 | Ward | 623/1.16 |
| 2005/0251259 A1 * | 11/2005 | Suddaby | 623/17.12 |
| 2005/0261781 A1 * | 11/2005 | Sennett et al. | 623/23.54 |
| 2006/0089715 A1 * | 4/2006 | Truckai et al. | 623/17.11 |
| 2006/0100706 A1 * | 5/2006 | Shadduck et al. | 623/17.11 |
| 2006/0106459 A1 * | 5/2006 | Truckai et al. | 623/17.11 |
| 2006/0293750 A1 * | 12/2006 | Sherman et al. | 623/17.12 |
| 2007/0043440 A1 * | 2/2007 | William et al. | 623/17.11 |
| 2007/0073397 A1 * | 3/2007 | McKinley | 623/17.11 |
| 2007/0088436 A1 * | 4/2007 | Parsons et al. | 623/17.11 |
| 2007/0093899 A1 * | 4/2007 | Dutoit et al. | 623/17.11 |
| 2007/0162132 A1 * | 7/2007 | Messerli | 623/17.11 |
| 2007/0173939 A1 * | 7/2007 | Kim et al. | 623/17.11 |
| 2007/0282340 A1 * | 12/2007 | Malandain | 606/69 |
| 2007/0282443 A1 * | 12/2007 | Globerman et al. | 623/17.11 |
| 2008/0009792 A1 * | 1/2008 | Henniges et al. | 604/98.01 |
| 2009/0177206 A1 * | 7/2009 | Lozier et al. | 606/93 |

FOREIGN PATENT DOCUMENTS

| | | |
|---|---|---|
| WO | WO 02/30338 A1 | 4/2002 |
| WO | WO 03/003951 A1 | 1/2003 |
| WO | WO 03/007853 A1 | 1/2003 |
| WO | WO 2004/034924 A2 | 4/2004 |
| WO | WO 2004/047689 A | 6/2004 |

* cited by examiner

FIG. 27
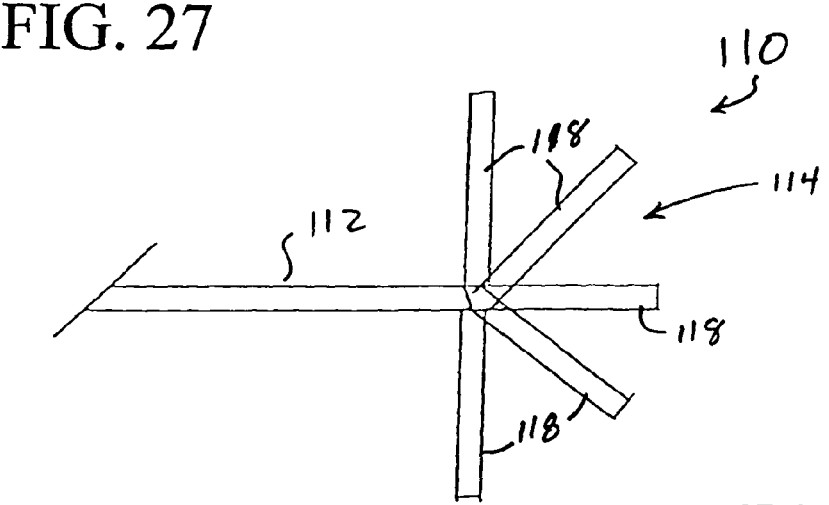
FIG. 28
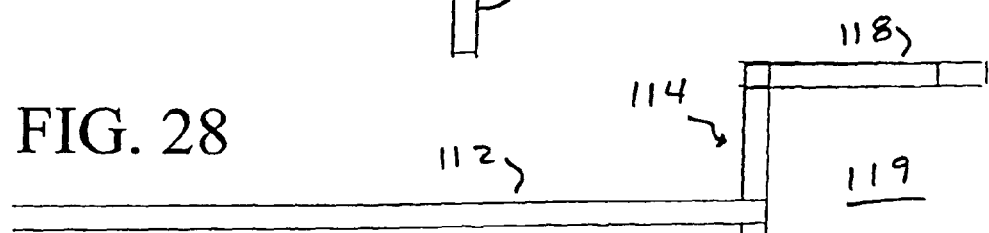
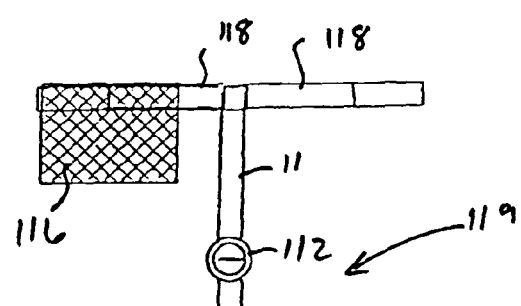
FIG. 29

IMPLANTABLE VERTEBRAL LIFT

FIELD OF THE INVENTION

This invention relates generally to vertebroplasty devices. More particularly, this invention relates to vertebroplasty lifts for restoration of compressed vertebral bodies and maintenance of height restoration and which are advantageously configured to inhibit migration of bone cement from outside a fracture area.

BACKGROUND AND SUMMARY OF THE INVENTION

Vertebroplasty and kyphoplasty are surgical procedures for treating osteoporotic fractures and the like. In these procedures a cement-like material is introduced, as by injection, into the fractured bone, e.g., the vertebral body. A disadvantage of conventional vertebroplasty is that it generally does not result in restoration of the height of compressed vertebral bodies. Kyphoplasty includes additional steps prior to and after introduction of the cement-like material wherein an inflatable balloon tamp is placed within the fracture and inflated to support the bone at a desired dimension for introduction of the cement, with the tamp being removed before the cement is introduced. Kyphoplasty sometimes helps in regards to height restoration, but desires improvement in that it does not offer consistent results and is a more invasive and complicated procedure. Accordingly, improvement is desired in the treatment of fractures, and particularly in the treatment of compressed vertebral bodies where height restoration or maintenance is desired.

In accordance with one aspect, the invention relates to vertebral lift device. In a preferred embodiment, the device includes an expandable member made of a bio-compatible material and having a plurality of interconnected structural members. The expandable member has a first dimension for insertion thereof into a damaged vertebral body having a damaged dimension. The interconnected structural members of the expandable member are expandable to a second dimension substantially corresponding to dimensions of the vertebral body prior to its damage. The expandable member defines a void area within a periphery defined by the structural members when the expandable member is expanded to the second dimension for receiving a restoration agent. A covering configured to substantially cover the exterior of the expandable member is provided to inhibit leakage of the restoration agent received within the void area.

In another aspect, the invention relates to a method for restoring a vertebral body. In a preferred embodiment, the method includes the steps of introducing the covered expandable member into the damaged vertebral body with the expandable member configured in its first dimension; expanding the expandable member to its second dimension within the damaged vertebral body to substantially restore the vertebral body to its pre-damage dimensions; maintaining the expandable member in the vertebral body at its second dimension and introducing a restoration agent into the void area of the expandable member; maintaining the restoration agent within the expandable member to support the vertebral body at a restored state; and maintaining the expandable member in the vertebral body at its second dimension to assist the restoration agent in maintaining the dimensions of the vertebral body in the restored state.

BRIEF DESCRIPTION OF THE DRAWINGS

Further features of preferred embodiments of the invention will become apparent by reference to the detailed description of preferred embodiments when considered in conjunction with the figures, which are not to scale, wherein like reference numbers, indicate like elements through the several views, and wherein.

FIG. 27 is a top plan view of a vertebral lift device in accordance with a still further embodiment.

FIG. 28 is a side view of the device of FIG. 27.

FIG. 29 is a front view of the device of FIG. 27.

DETAILED DESCRIPTION

The invention relates to vertebral lift devices of various configurations for insertion into a vertebral body and which are operable to be expanded to substantially expand a fractured vertebral body to its pre-fracture dimensions during a surgical procedure wherein a preferably flowable bone treatment agent is introduced into the vertebral body. In this regard, it will be understood that the bone treatment agent may be a variety of materials suitable for supporting a vertebral body, such as bone cement, microspheres, gels, and the like. In addition to conventional bone cement, a preferred restoration agent is a flowable material having microparticulates of a pre-set or polymerized hydrogel material dispersed within a carrier, as described in U.S. application Ser. No. 10/987,817, entitled HYDROGEL BONE VOID FILLER and filed concurrently herewith.

The lift devices of the invention may be left within the vertebral body to help maintain the vertebral body at the desired restored expanded condition. The lift devices are also desirably configured to include a covering to help retain the bone cement or other agent in desired locations and to otherwise inhibit undesirable post introduction migration bf the bone cement.

Figure 2:
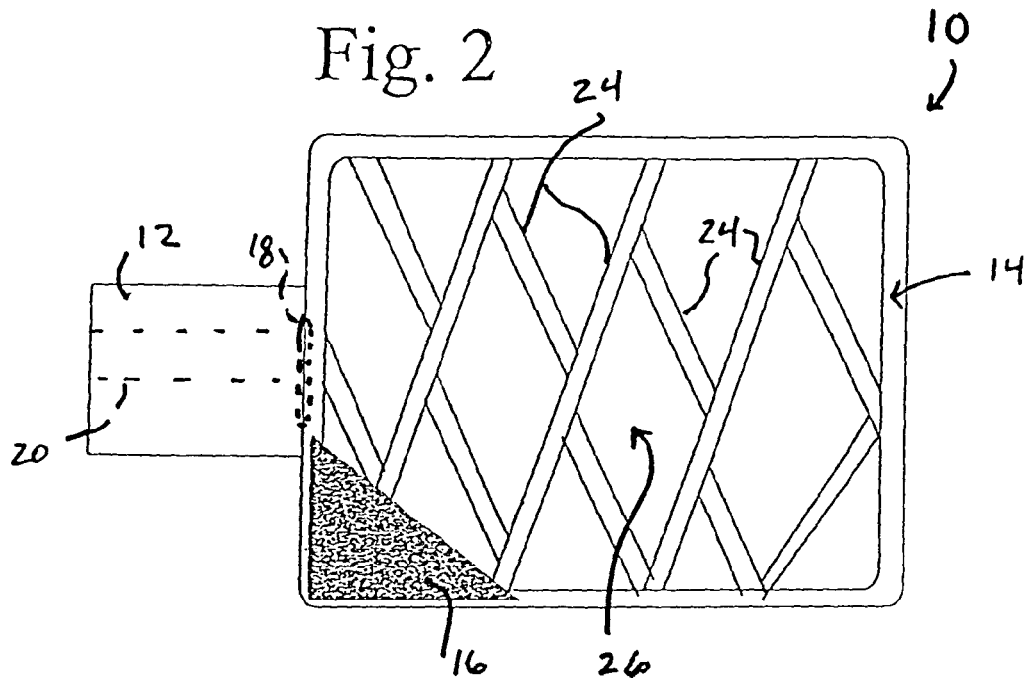
FIG. 2 is a side view of the device of FIG. 1 shown in an expanded state.
Figure 1:
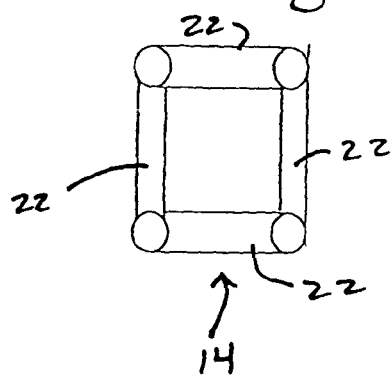
FIG. 1 is a front view of a vertebral lift device in accordance with a preferred embodiment of the invention.
Figure 3:
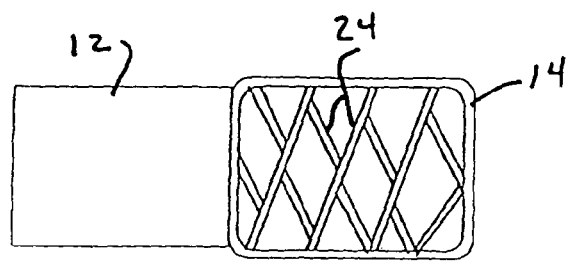
FIG. 3 is a side view of the device of FIG. 1 shown in an unexpanded state.

In one preferred embodiment, and with reference to FIGS. 1-3, the invention relates to a vertebral lift 10 having an introduction member 12 and an expandable member 14. A covering 16 is provided to cooperate with the expandable member 14 to inhibit leakage of bone cement or other bone treatment agent introduced during a surgical procedure corresponding to use of the device 10 to repair a fractured vertebral body.

The introduction member 12 preferably provided by an elongate mandrel of metal, plastic, or other polymeric material configured in dimension to be received through the lumen of a conventional bone needle. The member 12 cooperates with the expandable member 14 for expansion and/or detachment thereof. For example, the member 12 may be rotated to introduce rotational forces to the member 14 for expansion purposes and to detach the introduction member 12 and the expandable member 14 from engagement with one another. Alternatively, the introduction member 12 may be utilized to push or pull on the expandable member 14 to expand it.

In the case of the expandable member 14 having kinetic expansion forces, such as being made of a spring material, a retention device may be utilized to retain the expandable member 14 in a compressed state and the introduction member 12 manipulated to release the retention device to allow the expandable member 14 to expand. In this regard, it will be understood that "expansion" includes radial expansion or elongate expansion or both and including other growth in dimension as may be involved as the expandable body enlarges in a manner to correspond to the desired restored dimensions of the vertebral body.

The expandable member may also be made of a thermally active material that undergoes significant expansion or contraction when exposed to body temperatures. For example, shaped memory alloys, such as nickel and titanium allows exhibit significant contraction when exposed to body temperatures from an ambient temperature. This contraction can be used to release the expandable member from a compacted orientation and allow the components thereof to spring to an expanded orientation.

A coupling 18 is preferably provided to detachably couple the introduction member 12 and the expandable member 14. For example, the coupling member 18 may be configured to be thermally activated, e.g., to expand, contract, dissolve, or degrade, or example, in the presence of a predetermined thermal condition to accomplish desired detachment of the introduction member and the expandable member 14. An example of such a coupling member is described in connection with FIG. 35. The coupling member 18 may also enable mechanical separation, wherein the coupling member is mechanically manipulated to detach from the expandable member 14, such as described in connection with FIG. 36.

The introduction member 12 also preferably includes a flow path 20 such as an internal channel for introducing bone cement into the interior portions of the expandable member 14 to provide the bone cement to desired locations within a vertebral body.

The expandable member 14 is configured to have sufficiently small dimensions in an unexpanded state so as to allow it to be introduced by the introduction member 12 to a vertebral body through a bone needle. The expandable member 14 is preferably of substantially rectangular configuration and includes a peripheral expandable frame 22 and a plurality of interconnected expandable spanning members 24 that connect between the edges of the frame 22.

The expandable member 14 is operable to be expanded once it is desirably positioned in a vertebral body so as to sufficient dimensions and strength to expand a fractured vertebral body to dimensions corresponding substantially to the pre-fracture dimensions of the vertebral body. In this regard, the expandable member 14 may be expanded by mechanical forces, such as rotational forces imparted thereto by the introduction member 12, or as by thermal action, wherein the material from which the expandable member 14 is formed expands when exposed to a threshold temperature, such as the internal body temperatures of a patient. Examples of preferred materials include degradable and non-degradable metals and polymers which are sufficiently non-toxic so as to enable the expandable member 14 to be left within the vertebral body following the surgery.

The covering 16 is preferably a bio-compatible polymeric elastomer mesh or metal mesh material that is configured to substantially cover the exterior of the expandable member 14 to inhibit bone cement or the like introduced into a void area 26 of the expanded member 14 from leaking out of the void area 26. Preferred materials include polyester and nickel/titanium alloys (e.g. nitinol) having a silicon or other elastomeric coating to facilitate elasticity of the mesh and promote self-sealing properties. The void area 26 is defined by the periphery of the structure provided by the frame 22 and spanning members 24 and around which the covering 16 is disposed.

The covering 16, for example, may be an interwoven expandable polymer material which allows for cell infiltration, yet maintains injected material, such as bone cement, within its confines. Thus, while in the various views herein coverings are only partially depicted for clarity purposes, it will be understood that the coverings preferably substantially cover encloses the expandable member with which they are associated.

Accordingly, in a desired method or use of the device 10 to restore a fractured vertebral body, the expandable member 14 having the covering 16 and attached to the introduction member 12 is introduced to a desired location within the vertebral body by manipulation of the introduction member 12. The expandable member 14 is then expanded, as by manipulation of the introduction member 12 or by exposure to desired thermal conditions. Bone cement is then introduced into the void area 26 of the expanded member 14, preferably via the introduction member 12, and the cement cures to a hardened state. The introduction member 12 is then detached from the expandable member 14 and the expandable member 14 is left in the vertebral body in the expanded state with the injected bone cement maintained within the expandable member 14 by the covering 16.

Figure 4:
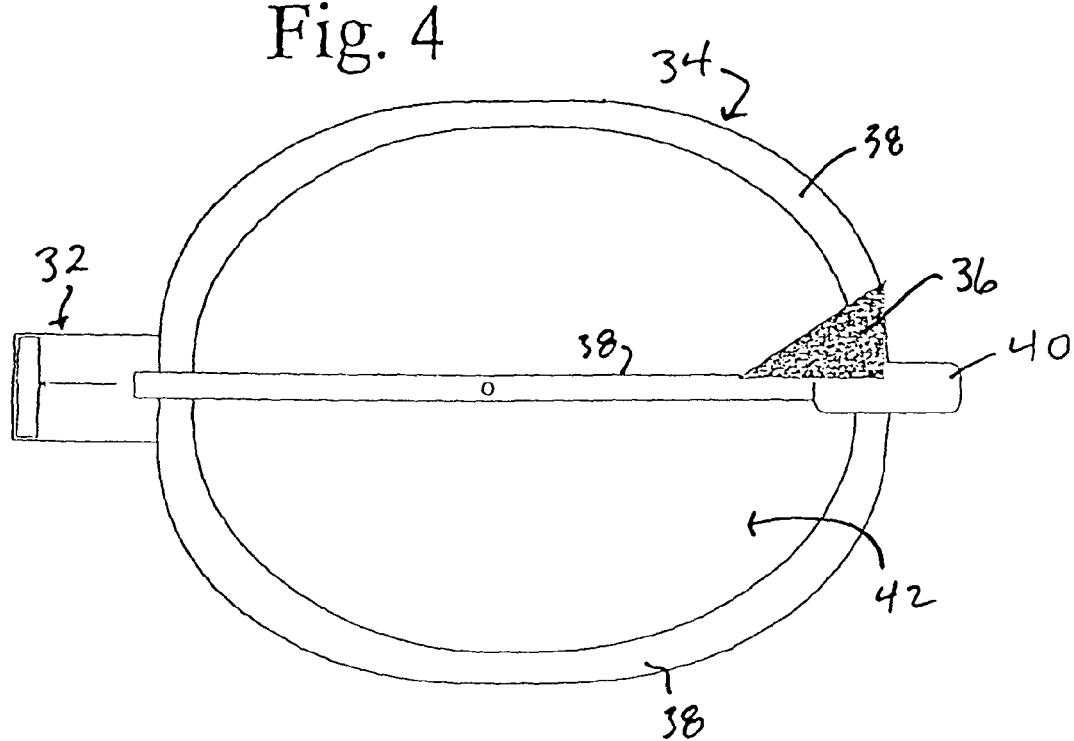
FIG. 4 is a side view of a vertebral lift device in accordance with an alternate embodiment of the invention.
Figure 5:
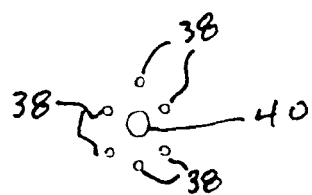
FIG. 5 is an end view of the device of FIG. 4.

With reference to FIGS. 4 and 5, there is shown an alternate embodiment of a vertebral lift 30 having an introduction member 32 and an expandable member 34. A covering 36 is preferably provided to cooperate with the expandable member 34 to inhibit leakage of bone cement. The introduction member 32 and the covering 36 are preferably substantially identical to the introduction member 12 and the covering 16.

The expandable member 34 is preferably operable in the same manners as described for the expandable member 14. The expandable member 34 is preferably of substantially egg-shaped or ovaloid configuration and includes a plurality of arched expandable ribs 38. An elastomeric bumper tip 40 is preferably provided at the terminal end of the expandable member 34 to minimize trauma during introduction of the expandable member 34 into a vertebral body. A void area 42 is defined within the expandable member 34 for receiving bone cement or the like in the manner of the void area 26.

Figure 6:
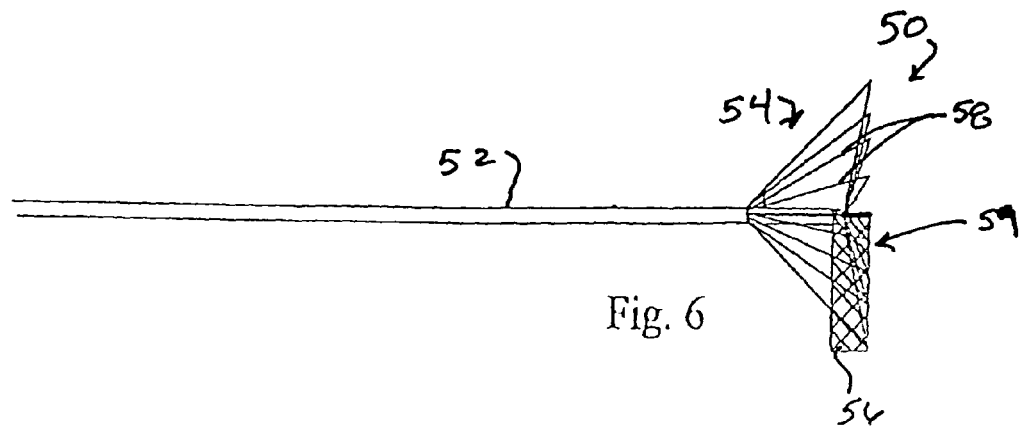
FIG. 6 is a side view of another embodiment of a vertebral lift device, shown in an expanded state.
Figure 7:
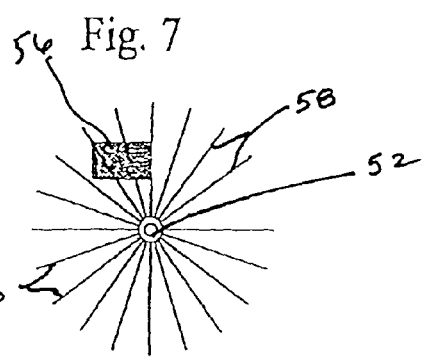
FIG. 7 is an end view of the device of FIG. 6.

With reference to FIGS. 6 and 7, there is shown an alternate embodiment of a vertebral lift 50 having an introduction member 52 and an expandable member 54. A covering 56 is preferably provided to cooperate with the expandable member 54 to inhibit leakage of bone cement. The introduction member 52 and the covering 56 are preferably substantially identical to the introduction member 12 and the covering 16.

The expandable member 54 is preferably operable in the same manners as described for the expandable member 14. The expandable member 54 is preferably configured as an inverted cone or umbrella shape and includes a plurality of expandable ribs 58. A void area 59 is defined within the expandable member 54 for receiving bone cement or the like in the manner of the void area 26.

Figure 8:
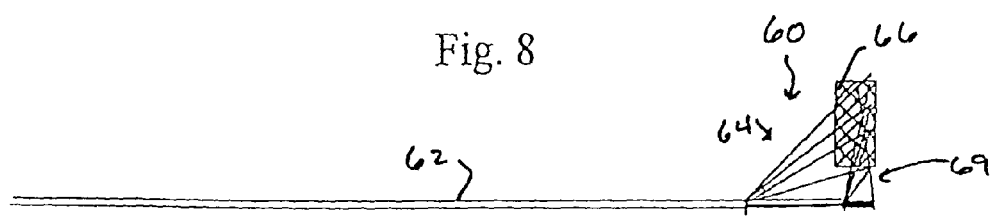
FIG. 8 is a side view of still another embodiment of a vertebral lift device, shown in an expanded state.
Figure 9:
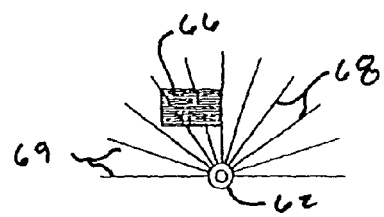
FIG. 9 is an end view of the device of FIG. 8.
Figure 11:
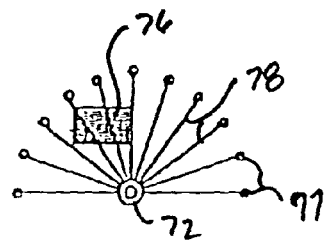
FIGS. 10 and 11 are side and end views, respectively, of a modified version of the device of FIGS. 8 and 9.
Figure 10:
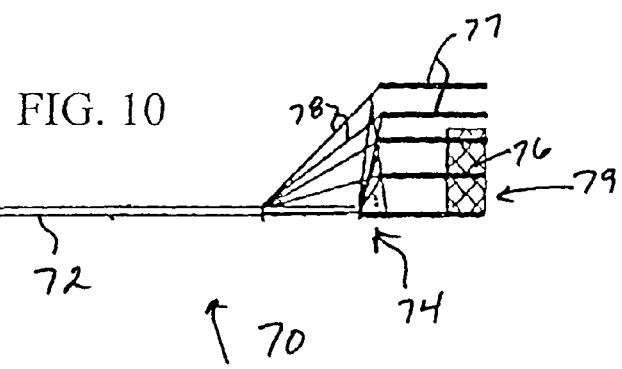
Figure 12:
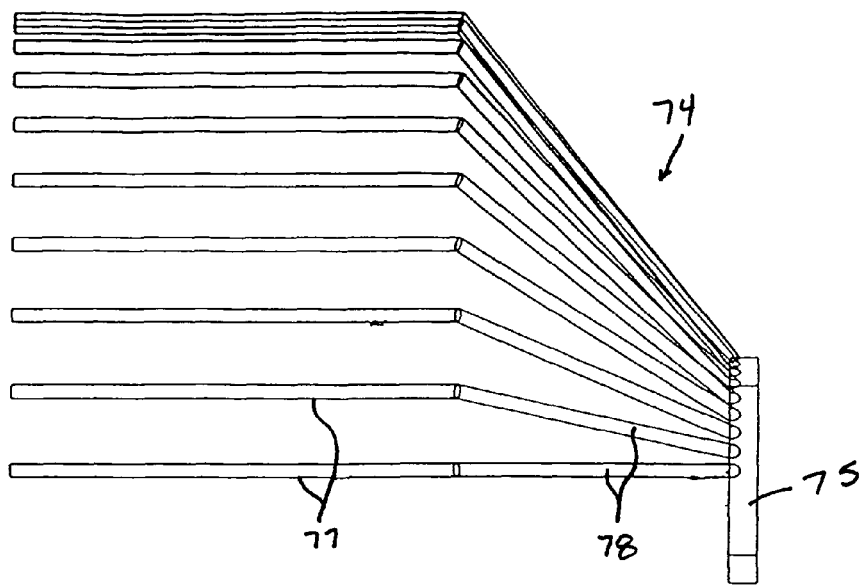
FIGS. 12 and 13 are side and perspective views, respectively, of an expandable member of the device of FIGS. 10 and 11.
Figure 13:
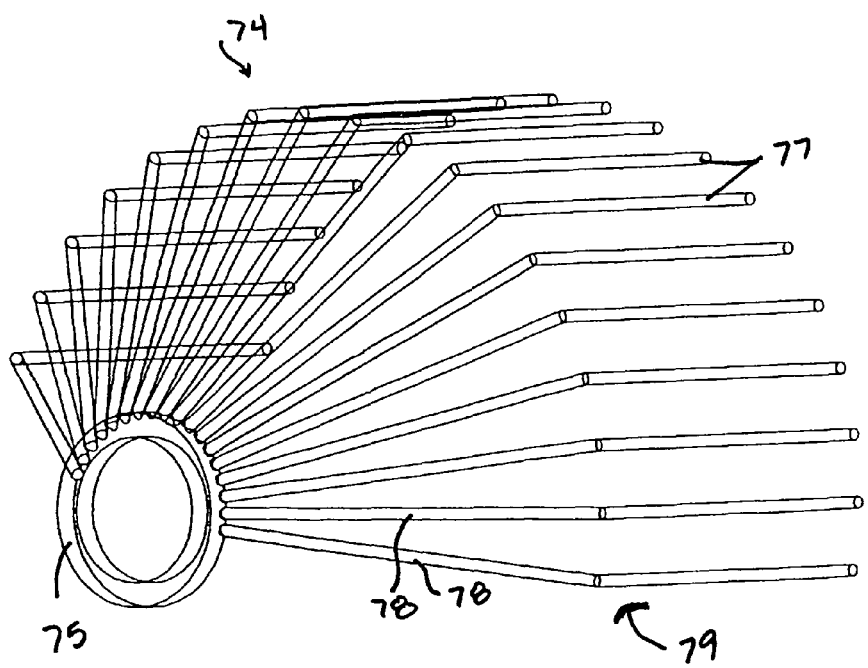

With reference to FIGS. 8 and 9, there is shown an alternate embodiment of a vertebral lift 60 having an introduction member 62 and an expandable member 64. A covering 66 is preferably provided to cooperate with the expandable member 54 to inhibit leakage of bone cement. The vertebral lift 60 is similar to the vertebral lift 50, except that it has a half-cone shape instead. The expandable member 64 includes a plurality of expandable ribs 68 and defines a void area 69.

With reference to FIGS. 10-13, there is shown an alternate embodiment of a vertebral lift 70 having an introduction member 72, an expandable member 74, and a covering 76. The vertebral lift 70 includes a plurality of expandable ribs 78 extending from a ring member 75 and defines a void area 79 and is similar to the vertebral lift 60 except that it further includes lateral ribs 77.

Figure 14:
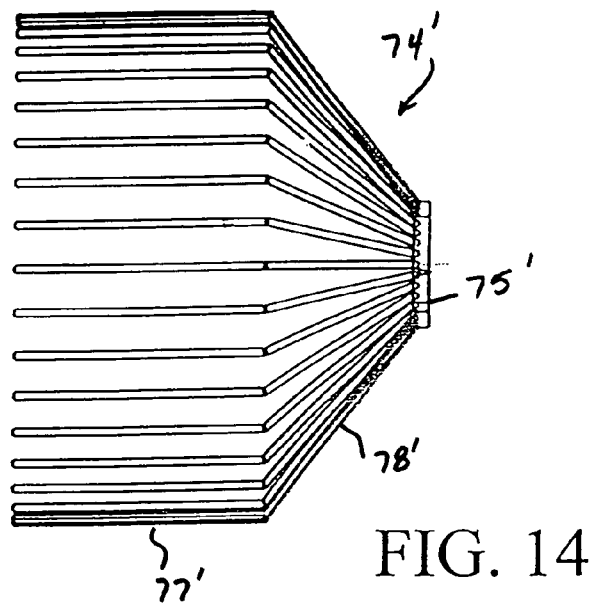
FIGS. 14 and 15 are side and end views, respectively, of a modified version of the device of FIGS. 6 and 7.
Figure 15:
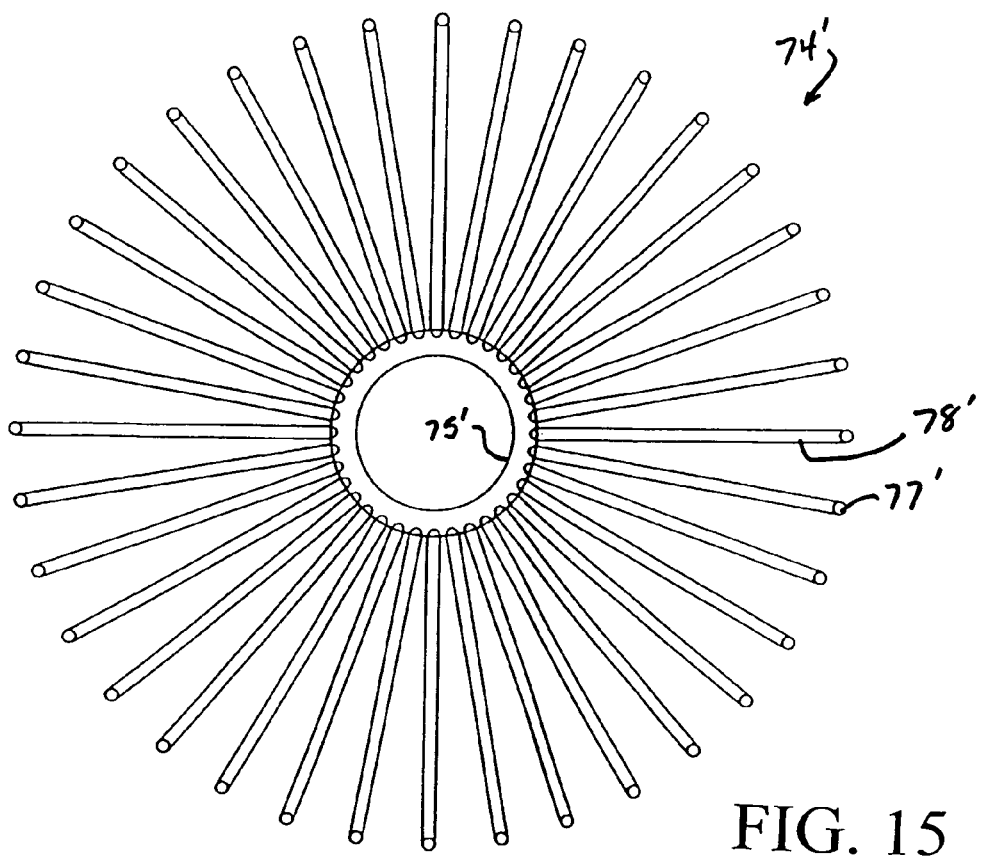

FIGS. 14 and 15 show an alternate embodiment of an expandable member 74' that is similar to the expandable member 74, except that it includes expandable ribs 78' and accompanying lateral ribs 77' completely around ring member 75'.

Figure 16:
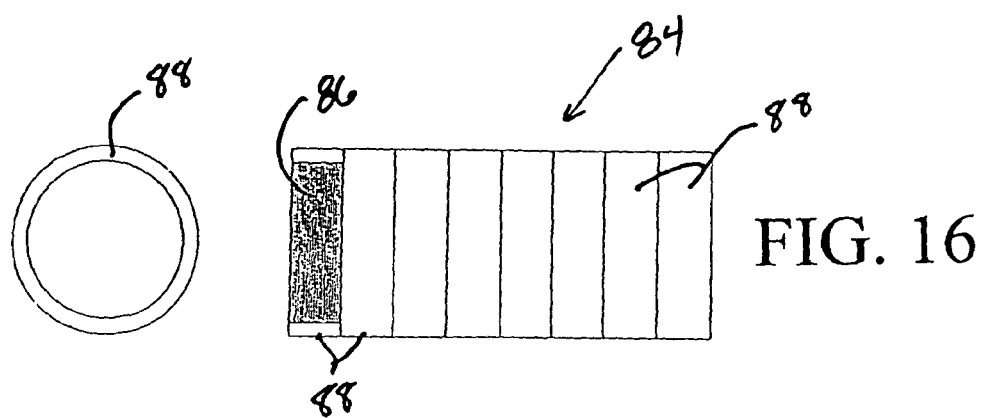
FIG. 16 is a side view of a lift device having a plurality of ring members in accordance with yet another embodiment of the invention.
Figure 17:
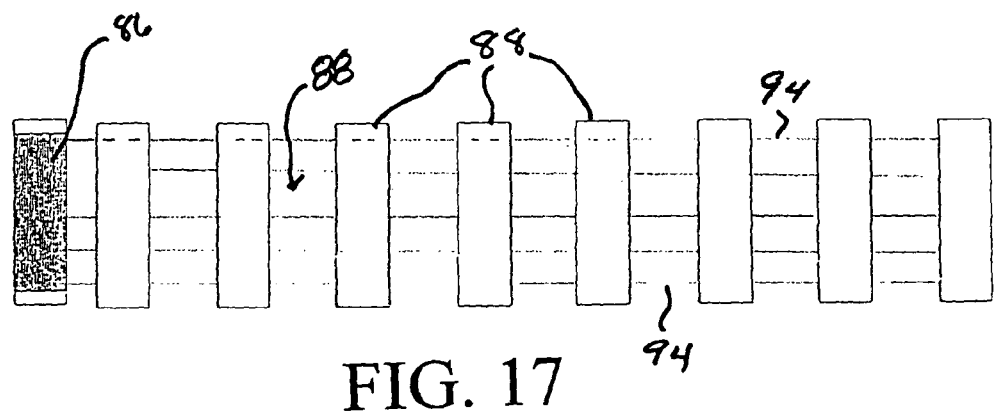
FIG. 17 shows the device of FIG. 16 in an elongated state.

With reference to FIGS. 16 and 17, there is shown an alternate embodiment of an expandable member 84 having a covering 86 to inhibit leakage of bone cement. The expandable member 84 preferably cooperates with an introduction member, such as the introduction member 12 described previously, for desirably expanding the expandable member 84 to desired dimensions for restoration of the fractured vertebral body into which it is installed.

The expandable member 84 preferably includes a plurality of rings 88 oriented in an end-to-end fashion to provide the expandable member 84 with a generally cylindrical configuration which defines an internal annular void area 90 for receiving bone cement. FIG. 17 shows the expandable member 84 with the rings 88 expanded by elongation, with the rings 88 substantially uniformly spaced apart. It will be understood, however, that the rings may be non-uniformly spaced apart and/or the uniformly or non-uniformly enlarged by diametrical expansion.

Figure 18:
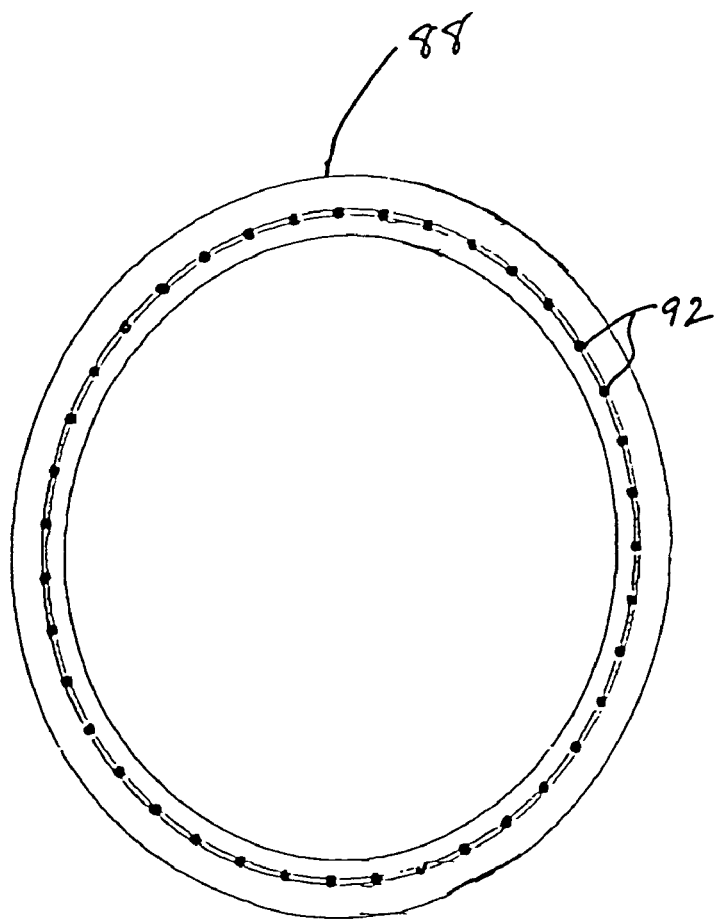
FIG. 18 is a detailed view of a ring member component of the device of FIGS. 16 and 17.

In this regard, and with additional reference to FIG. 18, there is shown an enlarged view of one of the rings 88. The ring 88 preferably includes a plurality of apertures 92 which extend through the thickness of the ring 88 and configured for receiving wires 94 (FIG. 17) or other elongate members which may be manipulated to retain the expandable member 84 in a desired state of expansion.

Figure 19:
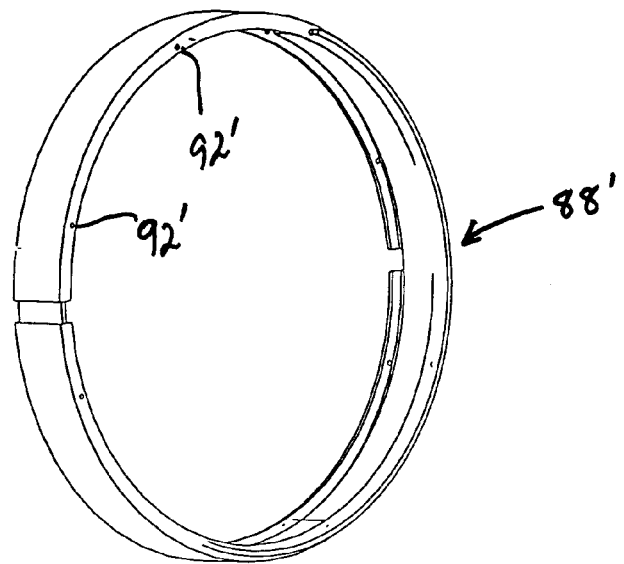
FIGS. 19 and 20 are perspective and end views, respectively, of another embodiment of a ring member.
Figure 20:
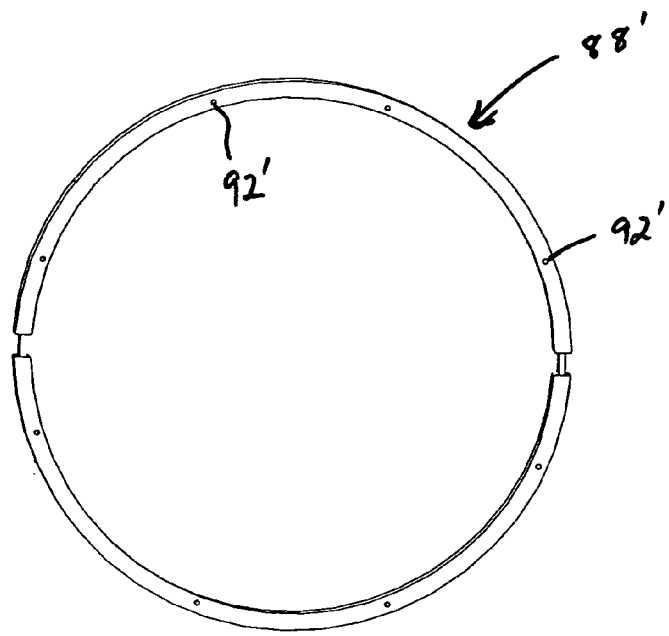
Figure 21:
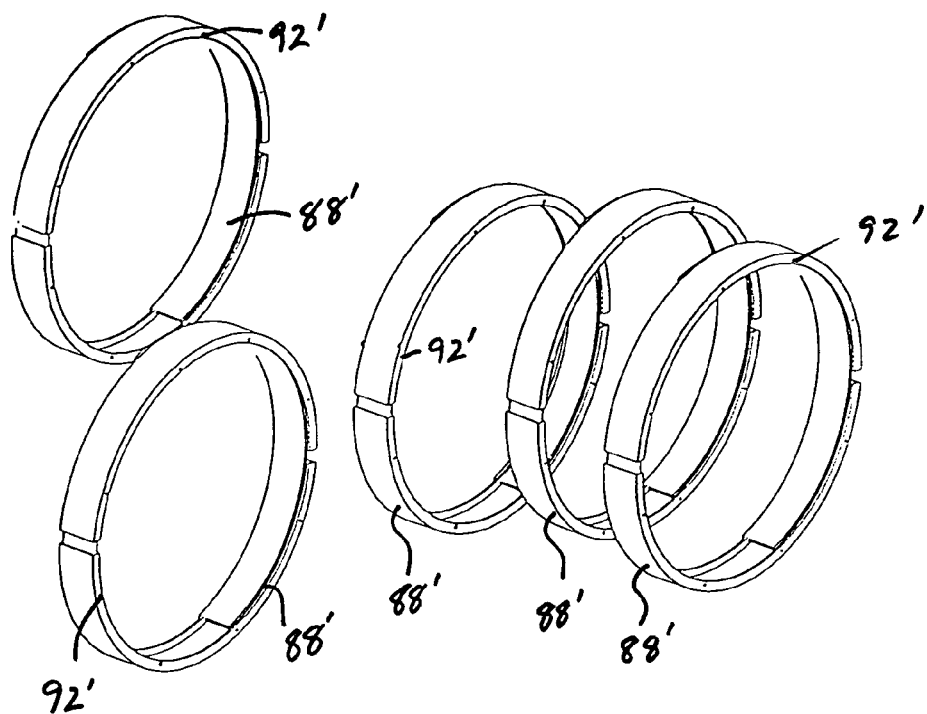
FIGS. 21 and 22 are perspective and end views, respectively, of a lift device having a plurality of the ring members of FIGS. 19 and 20, and configured in an expanded and elongated state.
Figure 22:
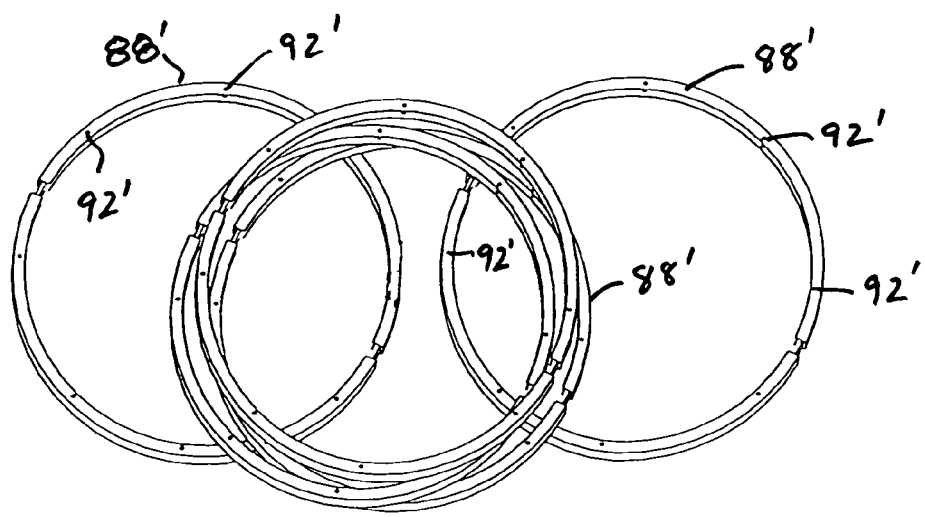
Figure 23:
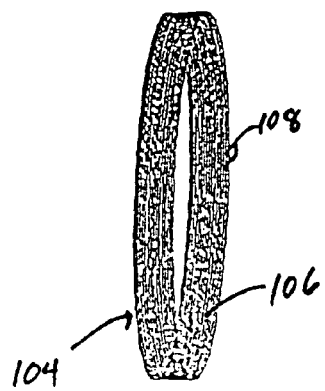
FIG. 23 is a side perspective view of still another embodiment of a lift device provided by a coiled member.

FIGS. 19 and 20 show an alternate embodiment of a ring 88' that is useful in the same manner as the ring 88 and includes apertures 92' for receiving wires, such as the wires 94. FIGS. 21 and 22 are perspective and end views, respectively, showing how the rings 88' may be positioned in an expanded and elongated orientation in a vertebral body, with the wires 94 which would extend through the apertures 92 omitted for clarity.

With reference to FIGS. 23, 24, 25 and 26, there is shown an alternate embodiment of an expandable member 104 having a covering 106 to inhibit leakage of bone cement from an internal annular void area 102. The expandable member 104 preferably cooperates with an introduction member, such as the introduction member 12 described previously, for desirably expanding the expandable member 104 to desired dimensions for restoration of the fractured vertebral body into which it is installed.

Figure 24:
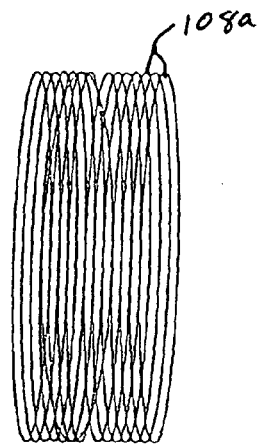
FIGS. 24 and 25 show variations of the device of FIG. 23 wherein the range of coil dimensions is illustrated.
Figure 25:
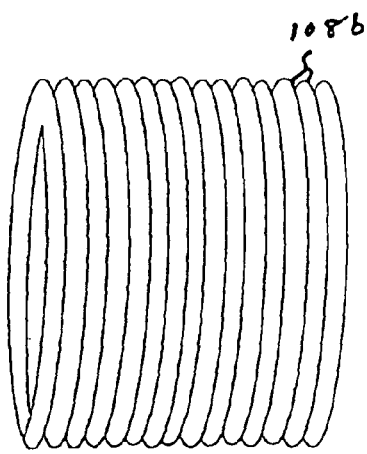
Figure 26:
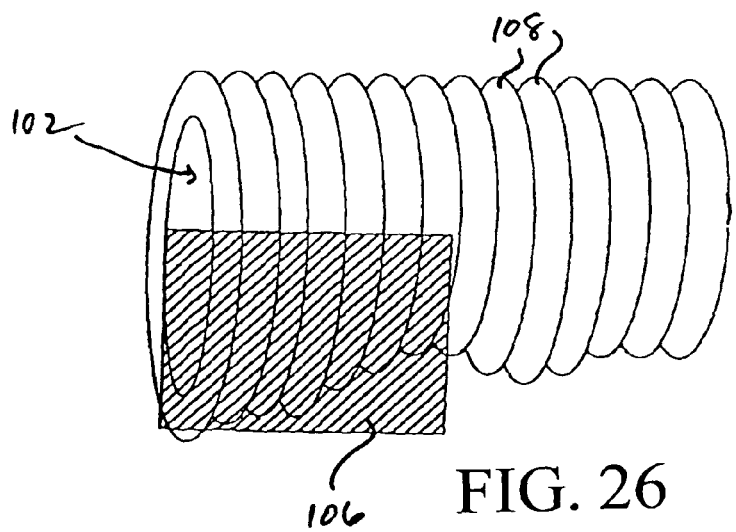
FIG. 26 shows the device of FIG. 25 elongated and expanded to provide differing coil diameters along the length of the device as may occur when expanding the device within a vertebral body.

The expandable member 104 is preferably configured as a coiled member and includes a plurality of interconnected coils 108. FIGS. 24 and 25 show examples of the coils having different dimensions. For example, coils 108a shown in FIG. 24 are thinner than coils 108b shown in FIG. 25. FIG. 26 shows the expandable member 104 with the coils 108 non-uniformly expanded, wherein the diameters of various ones of the expanded coils are different. As will be appreciated, this flexibility is particularly suitable for use in restoration of non-uniform vertebral dimensions.

Figure 30:
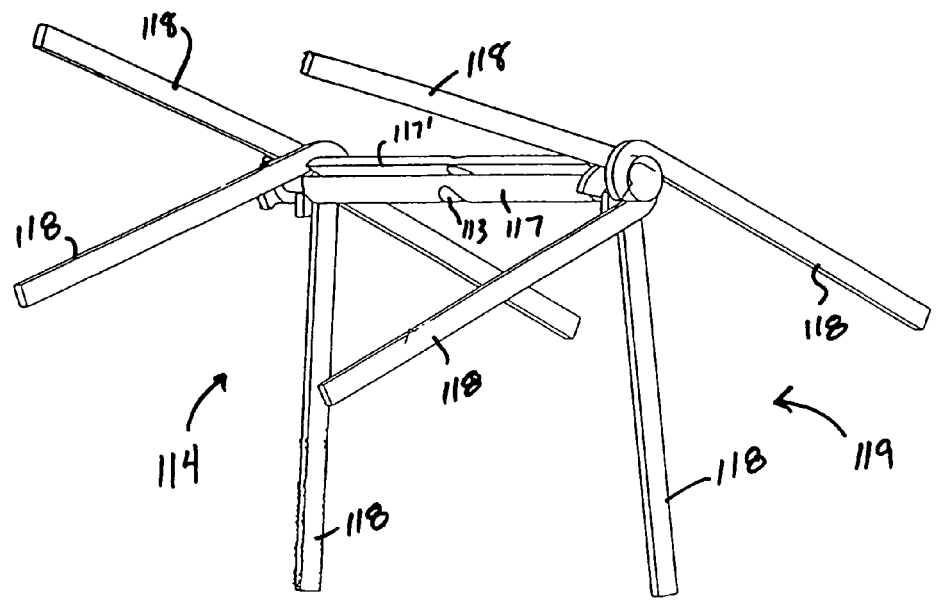
FIGS. 30 and 31 are perspective views of an expandable member component of the device of FIG. 27.
Figure 31:
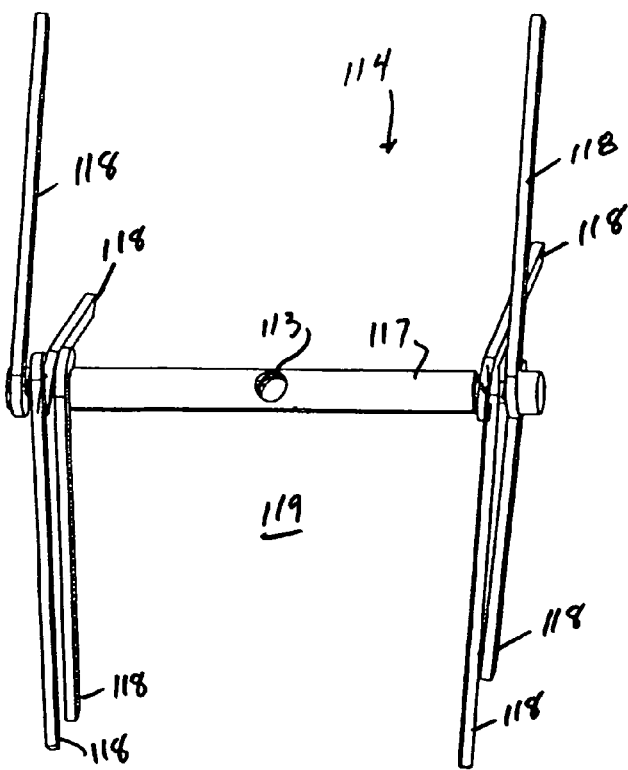

With reference to FIGS. 27-29, there is shown an alternate embodiment of a vertebral lift 110 having an introduction member 112 and an expandable member 114. The introduction member 112 may attach to either end of the member 114, or more preferably, to an aperture 113 defined thereon (FIGS. 30 and 31). A covering 116 is preferably provided to cooperate with the expandable member 114 to inhibit leakage of bone cement. The introduction member 112 and the covering 116 are preferably substantially identical to the introduction member 12 and the covering 16.

With additional reference to FIGS. 30-31, the expandable member 114 is preferably operable in the same manners as described for the expandable member 14. The expandable member 114 includes a plurality of expandable struts 118 which project from a lateral member 117 to define a void area 119 for receiving bone cement or the like in the manner of the void area 26. As will be appreciated, the covering 116 substantially encloses the void area 119 to retain the injected bone cement within the area 119.

The struts 118 preferably are received within a groove 117' of the lateral member 117 for introduction of the member 114 into a vertebral body, with the struts 118 opening from the groove 117' to the orientation as shown in FIGS. 30-31 when exposed to the elevated temperature of the patient within the vertebral body. In this regard, the expandable member 114 is preferably made of a nickel and titanium alloy (e.g. nitinol) which significantly contracts when exposed to body temperature (coming from an ambient environment). Thus, the material used to make the expandable member 114 will contract once placed in the vertebral body, causing the struts 118 to be released from the groove 117' and thereby spring or expand to the orientation shown in FIGS. 30 and 31. Thus, while the material from which the expandable member 114 is made actually contracts within the vertebral body, the overall dimension of the expandable member 114 is increased as the struts 118 are released from the compacted state within the groove 117'.

Figure 32:
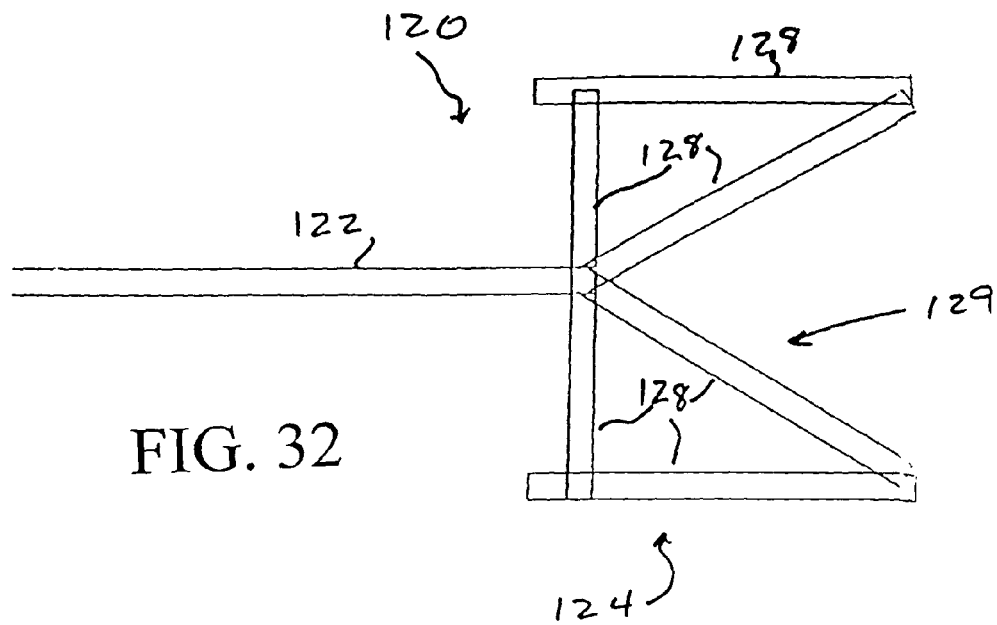
FIG. 32 is a side view of a vertebral lift device in accordance with yet another embodiment.
Figure 33:
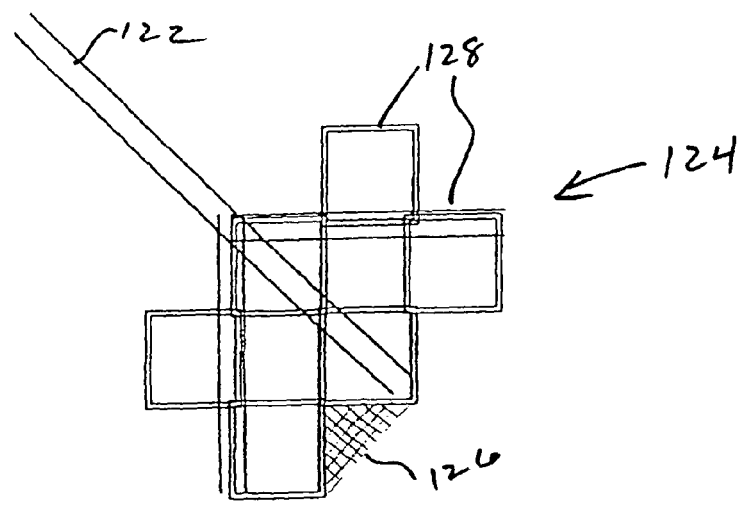
FIG. 33 is a top view of the device of FIG. 32.

With reference to FIGS. 32 and 33, there is shown an alternate embodiment of a vertebral lift 120 having an introduction member 122 and an expandable member 124. A covering 126 is preferably provided to cooperate with the expandable member 124 to inhibit leakage of bone cement. The introduction member 122 and the covering 126 are preferably substantially identical to the introduction member 12 and the covering 16.

Figure 34:
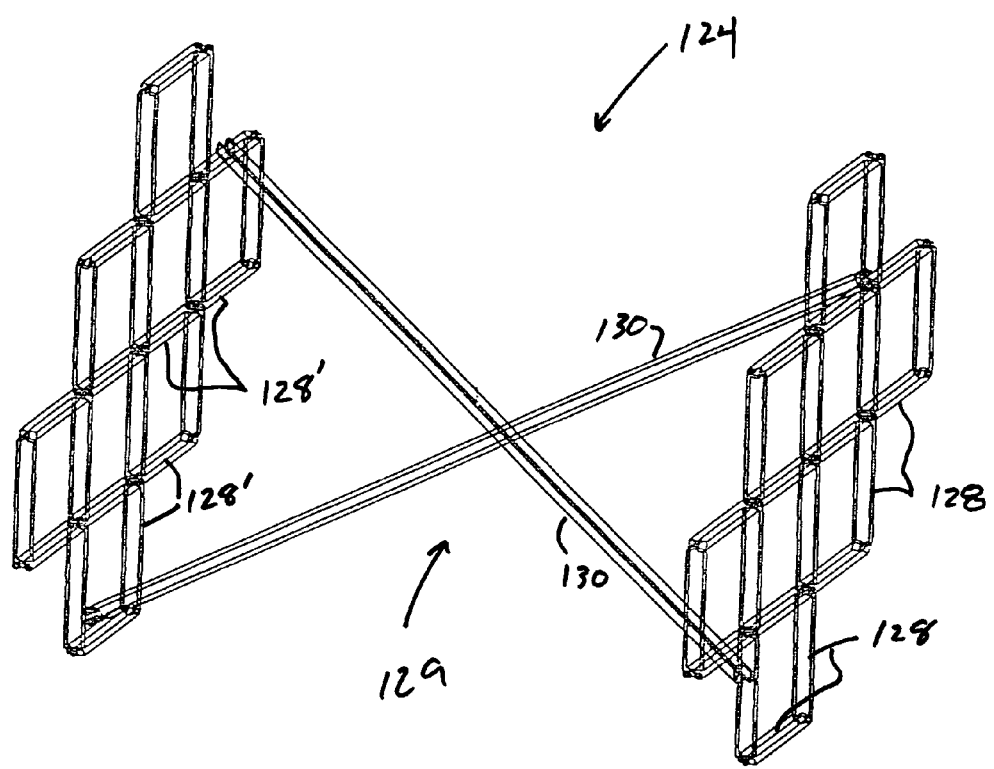
FIG. 34 is a perspective view of an expandable member component of the device of FIG. 32.

With additional reference to FIG. 34, the expandable member 124 is preferably operable in the same manners as described for the expandable member 14. The expandable member 124 is preferably a jointed extensible framework and includes a first plurality of interconnected frame members 128 and a second set of interconnected frame members 128' which cooperate to define a void area 129 for receiving bone cement or the like in the manner of the void area 26. The sets of frame members 128 and 128' are spaced apart by spanning members 130. Thus, the expansion of the expandable member 124 is defined by the expansion of the sets of frame members 128 and 128' as well as the spanning members 130.

Figure 35:
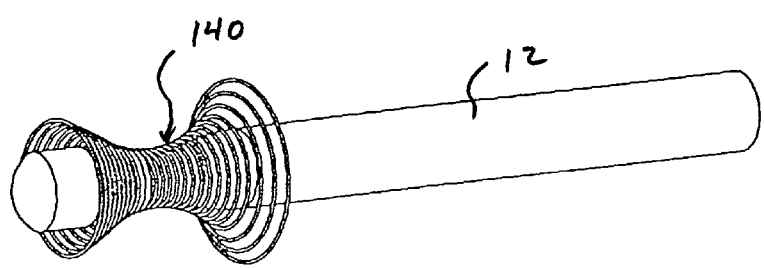
FIG. 35 is a perspective view of an introduction member and an associated coupling.

With reference now to FIG. 35, there is shown a preferred embodiment of a thermal activated coupling member 140 which may be used to provide the coupling 18 described previously. In this embodiment, the coupling member 140 is provided in a coiled configuration and made of a shaped memory alloy, most preferably a nickel and titanium alloy such as nitinol. Nitinol contracts when heated and produces a much greater thermal movement (expansion, contraction) than standard metals. Thus, in a preferred embodiment, the coupling member 140 is disposed around the introduction member 12, with a free end 142 thereof engaged with a portion of the expandable member 14.

For example, the free end 142 may engage the aperture 113 of the expandable member 114 of FIGS. 30 and 31 for introduction of the expandable member into the vertebral body. Upon exposure to the elevated temperature within the vertebral body, the coupling member will contract and disengage from the expandable member, thus enabling the introduction member 12 and the coupling member to be withdrawn from the patient, with the expandable member left in the vertebral body.

Figure 36:
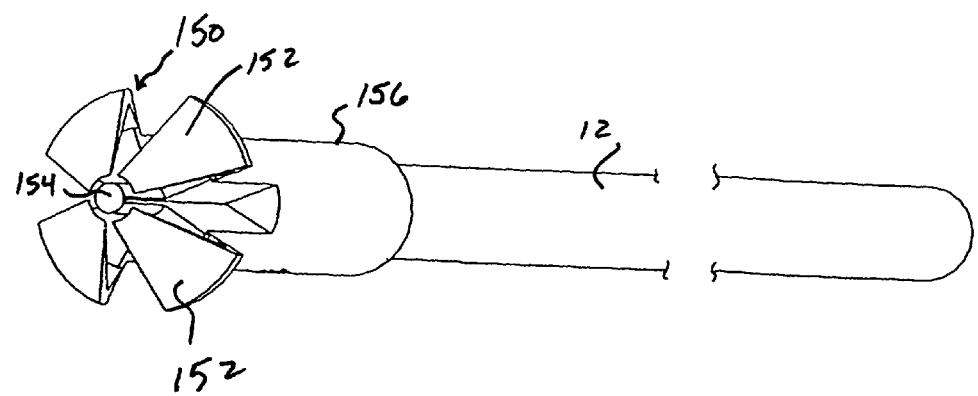
FIG. 36 shows an alternate embodiment of an introduction member and coupling.

With reference now to FIG. 36, there is shown a preferred embodiment of a mechanical coupling member 150 which may be used to provide the coupling 18 described previously. In this embodiment, the coupling member 150 has a plurality of fingers 152 surrounding a projection 154 (such as for mating with the aperture 113 of the member 114). A sleeve 156 is slidable upon the introduction member 12 to bear against the fingers 152 to urge them away from the expandable member to mechanically detach it from the projection 154.

The foregoing embodiments represent various vertebral lift devices suitably configured for insertion into a vertebral body and which are operable to be expanded to substantially expand a fractured vertebral body to its pre-fracture dimensions during a surgical procedure wherein a bone cement or the like is introduced into the vertebral body. The coverings associated with the devices advantageously inhibit leakage of bone cement materials and the expandable members are advantageously maintained within the vertebral body after the surgical procedure to provide additional structure to maintain the restored vertebral body.

In this regard, it will be realized that the devices may be configured in various dimensions and of various materials as may be suited for a particular application, with the selection of such dimensions and materials being readily ascertainable by one of ordinary skill in the art.

Accordingly, the foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A vertebral lift device, comprising an expandable member made of a bio-compatible material and having a plurality of interconnected structural members, with the expandable member having a first dimension for insertion thereof into a damaged vertebral body having a damaged dimension, the interconnected structural members of the expandable member being expandable to a second dimension substantially corresponding to dimensions of the vertebral body prior to its damage to substantially expand the fractured vertebral body to its pre-damage dimensions and thereby provide a void area within a periphery defined by the structural members when the expandable member is expanded to the second dimension for receiving a restoration agent; and a covering configured to substantially cover the exterior of the expandable member to inhibit leakage of the restoration agent received within the void area.

2. The device of claim 1, wherein the covering comprises a bio-compatible polymeric mesh or metal mesh material.

3. The device of claim 1, further comprising an introduction member detachably connectable to the expandable member for introduction of the expandable member into the damaged vertebral body.

4. The device of claim 3, wherein the introduction member defines a flow path in flow communication with the expandable body for introducing the restoration agent into the expandable member.

5. The device of claim 3, wherein the introduction member is operable to expand the expandable member.

6. The device of claim 1, wherein the structural members are individually expandable.

7. The device of claim 1, wherein the restoration agent comprises a bone cement or microspheres or a hydrogel material.

8. The device of claim 1, wherein expansion of expandable member expands upon exposure to a predetermined thermal condition.

9. A method for restoring a damaged vertebral body, comprising the steps of: providing an expandable member made of a bio-compatible material and having a plurality of interconnected structural members, with the expandable member having a first dimension for insertion thereof into the damaged vertebral body which has a damaged dimension, the interconnected structural members of the expandable member being expandable to a second dimension substantially corresponding to dimensions of the vertebral body prior to its damage, wherein the expandable member is operable to substantially expand the vertebral body to its pre-damage dimensions and thereby provide a void area within a periphery defined by the structural members when the expandable member is expanded to the second dimension for receiving a restoration agent, and a covering configured to substantially cover the exterior of the expandable member to inhibit leakage of the restoration agent received within the void area;

introducing the expandable member having the covering into the damaged vertebral body with the expandable member configured in its first dimension;

expanding the expandable member to its second dimension within the damaged vertebral body to substantially restore the vertebral body to its pre-damage dimensions;

maintaining the expandable member in the vertebral body at its second dimension and introducing a restoration agent into the void area of the covered expandable member;

maintaining the restoration agent within the covered expandable member to support the vertebral body at a restored state; and maintaining the covered expandable member in the vertebral body at its second dimension to assist the restoration agent in maintaining the dimensions of the vertebral body in the restored state.

10. The method of claim 9, wherein the restoration agent comprises a bone cement or microspheres or a hydrogel material.

11. A vertebral lift device, comprising an expandable member made of a bio-compatible material and having a plurality of interconnected individually expandable structural members, with the expandable member having a first dimension for insertion thereof into a damaged vertebral body having a damaged dimension, the interconnected structural members of the expandable member being expandable to a second dimension substantially corresponding to dimensions of the vertebral body prior to its damage, wherein the expandable member defines a void area within a periphery defined by the structural members when the expandable member is expanded to the second dimension for receiving a restoration agent; and a covering configured to substantially cover the exterior of the expandable member to inhibit leakage of the restoration agent received within the void area.

12. A vertebral lift device, comprising an expandable member made of a bio-compatible material and having a plurality of interconnected structural members, with the expandable member having a first dimension for insertion thereof into a damaged vertebral body having a damaged dimension, the interconnected structural members of the expandable member being expandable upon exposure to a predetermined thermal condition to a second dimension substantially corresponding to dimensions of the vertebral body prior to its damage, wherein the expandable member defines a void area within a periphery defined by the structural members when the expandable member is expanded to the second dimension for receiving a restoration agent; and a covering configured to substantially cover the exterior of the expandable member to inhibit leakage of the restoration agent received within the void area.

\* \* \* \* \*